United States Patent [19]
Curti et al.

[11] Patent Number: 4,563,478
[45] Date of Patent: Jan. 7, 1986

[54] METHOD OF TRANQUILIZING

[75] Inventors: Maria Curti, Torre D'Isola, Italy; Fernando Fussi, Fribourg, Switzerland

[73] Assignee: Hepar Chimie S.A., Fribourg, Switzerland

[21] Appl. No.: 737,902

[22] Filed: May 24, 1985

Related U.S. Application Data

[63] Continuation of Ser. No. 521,641, Aug. 9, 1983, abandoned, which is a continuation-in-part of Ser. No. 380,754, May 21, 1982, abandoned.

[30] Foreign Application Priority Data

May 26, 1981 [IT] Italy ................ 21960 A/81

[51] Int. Cl.$^4$ ............................................. A61K 31/195
[52] U.S. Cl. ..................................... 514/561; 514/547; 514/551; 514/563; 514/616; 560/169; 560/171; 562/561; 562/571; 564/160
[58] Field of Search ............... 514/547, 551, 563, 561, 514/616

[56] References Cited

U.S. PATENT DOCUMENTS

| | | | |
|---|---|---|---|
| 2,368,604 | 1/1945 | White | 562/571 |
| 2,469,317 | 5/1949 | Shokal | 560/171 |
| 2,562,198 | 7/1951 | McKinney | 562/571 |
| 2,607,797 | 8/1952 | McKinney | 560/171 |
| 3,278,478 | 10/1966 | Materson | 560/171 |

FOREIGN PATENT DOCUMENTS

| | | | |
|---|---|---|---|
| 47-5476 | 2/1972 | Japan . | |
| 608799 | 6/1978 | U.S.S.R. | 560/171 |

OTHER PUBLICATIONS

Morosawa, Bull. Chem. Soc. Japan, 36, pp. 179–183, (1963).
Madhav, J. Heterocycl. Chem., 17, pp. 1231–1235, (1980).
Yokoo, Nippon Kagaku Zasshi, 77, pp. 599–602, (1956).

*Primary Examiner*—Michael L. Shippen
*Attorney, Agent, or Firm*—Cushman, Darby & Cushman

[57] ABSTRACT

The invention relates to compounds possessing GABA-like sedative and tranquilizing activity, characterized by being of general formula:

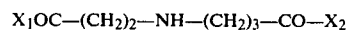

$$X_1OC-(CH_2)_2-NH-(CH_2)_3-CO-X_2$$

where
$X_1$ and $X_2$ are hydroxyl, a $C_1$–$C_6$ alkoxy group or a free or substituted amino group, $X_1$ being the same as or different from $X_2$.

The invention also relates to processes for their preparation, and composition for pharmaceutical and veterinary use which contains them.

2 Claims, No Drawings

METHOD OF TRANQUILIZING

This is a continuation of application Ser. No. 521,641, filed Aug. 9, 1983 (now abandoned), which is a C-I-P of Ser. No. 380,754 filed May 21, 1982, now abandoned.

This invention relates to a group of compounds with GABA-like activity and with predicted interesting application in the pharmaceutical and veterinary fields, principally as sedatives and tranquillisers, and generally in the treatment of hyperexcitability states in man and animals.

The physiological and metabolic part played by gamma-amino butyric acid (GABA) in inhibitory synaptic transmission in the CNS is known.

Any decrease in the cerebral levels of GABA caused by blockade of or congenital defects affecting the cerebral enzyme glutamic dehydrogenase (GLDH), which regulates the biosynthesis of GABA starting from glutamic acid, causes increased excitability of the nerve cells, with onset of a convulsive state. Conditions of cerebral GABA-depletion are obtained experimentally by administering semicarbizide or thiosemicarbizide (GLDH inhibitors) or other inhibitors, by induced Vitamin $B_6$ deficiencies, insulin shock, alkalosis.

In pathological conditions, decrease in cerebral levels of GABA causes convulsions and atonic or hypotonic loss of consciousness typical of epileptic seizures ("grand mal" and "petit mal").

Other neuropathological conditions are also, at least in part, ascribable to metabolic derangements of cerebral GABA. One problem involved in the use of GABA is connected with the fact that the substance does not cross the blood-brain barrier and consequently, when administered either orally or parenterally, does not reach the cerebral districts, or does so only to a minimal extent. A first object of the invention is to solve this problem. In this regard, according to the present invention, it has now been surprisingly found that the compounds of the formula given below possess a GABA-like anti-convulsant activity:

$$X_1OC-(CH_2)_2-NH-(CH_2)_3-CO-X_2 \quad (I)$$

where
$X_1$ and $X_2$ are hydroxyl, a $C_1-C_6$ alkoxy group, or a free or substituted amino group, $X_1$ being the same as or different from $X_2$.
and that said compounds, when administered parenterally, cross the blood-brain barrier and have said GABA-like effect in the CNS. According to the invention, this effect has for example been demonstrated by the protracting of the latency period of experimental convulsions induced by isoniazid and semicarbizide. The biochemical mechanism by which these substances act on reaching the brain is probably an enzymatic dissociation of the molecule, with liberation of active GABA.

Such mechanism clearly makes it possible to bypass the metabolic blockade—occurring in given pathological conditions—of the biosynthesis of GABA starting from the glutamic acid from the physiological amino acid pool.

Furthermore, the compounds of the invention have demonstrated to possess a surprising sedative and tranquillising activity which make them suitable for application in the pharmaceutical and veterinary fields generally in the treatment of hyperexcitability states. N-$\beta$-carboxyethyl-$\gamma$-aminobutyric acid (hereinafter referred to as CEGABA) is known in the literature of organic synthesis, and in Nippon Kagak Zasshi 77, 599–602 (1956) Akira Yokoo and Shiro Morosawa have described its synthesis.

There are, however, certain problems connected with this known synthesis; in particular it would be most desirable to obtain with it final products of greater purity, with higher processing yields and using a smaller number of reaction steps. A further object of the present invention is therefore to provide a process for the synthesis of compounds having GABA-like activity of said general formula (I), such as will obtain the aforesaid desirable advantages as compared to the known art.

To obtain this object the present invention provides a process for preparing said compounds of general formula (I) characterized by condensing a substrate chosen from: $\gamma$-aminobutyric acid (II) indicated hereinafter as GABA), its pyrrolidin-2-one lactam (II)', or its amides or esters, with a reagent chosen from: acrylonitrile, acrylic acid, or its esters or amides.

Reaction schemes are given hereinafter relative to possible preferred embodiments of the process according to the invention as substantially defined heretofore.

SCHEME A

Condensation of $\gamma$-aminobutyric acid (II) with acrylonitrile (III), followed by hydrolysis to give N-$\beta$-carboxyethyl-$\gamma$-aminobutyric acid (V).

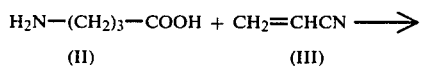

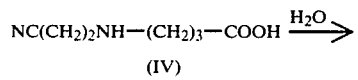

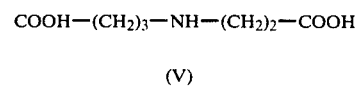

SCHEME A'

Condensation in accordance with Scheme A, starting from pyrrolidin-2-one lactam (II)', comprising the opening of the ring to give (II).

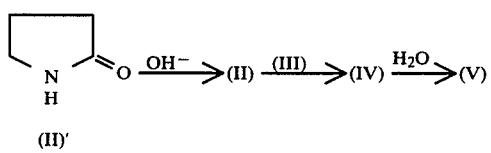

SCHEME B

Condensation of (II) with acrylic acid (VI) or with one of its esters (VII), to give the acid (V) or one of its monoesters (VIII) respectively.

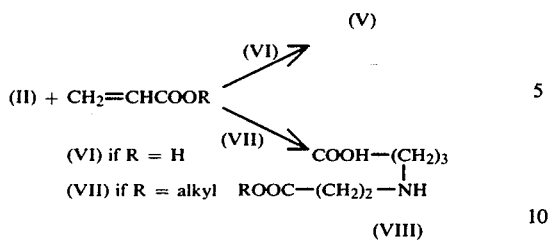

SCHEME C

Esterification of (II) to give the ester (XI), followed by condensation with (VI) or (VII) to give the monoester (IX) or the diester (X) of the acid (V) respectively.

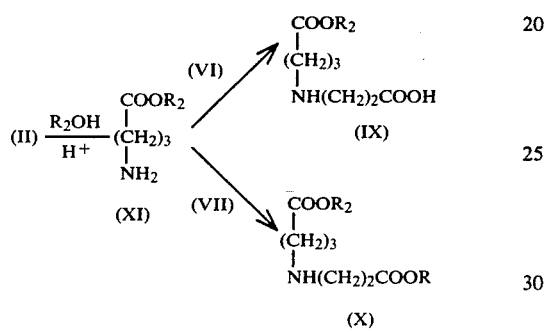

SCHEME D

Esterification of (V) to give the corresponding diester

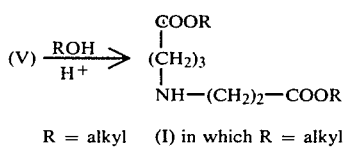

R = alkyl   (I) in which R = alkyl

SCHEME E

Condensation of γ-aminobutyramide (XII) with acrylonitrile, followed by partial hydrolysis to amidoethyl-γ-aminobutyramide (XIV) by way of (XIII).

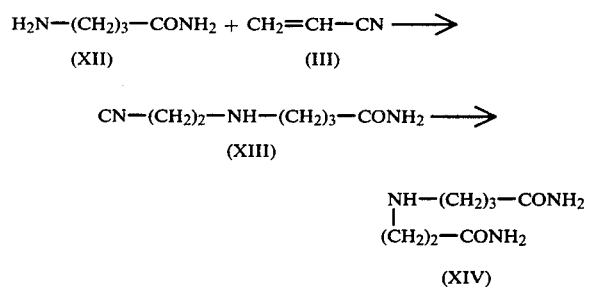

SCHEME F

Condensation of γ-aminobutyric acid (II) with acrylonitrile followed by partial hydrolysis to amidoethyl-γ-aminobutyric acid (XV).

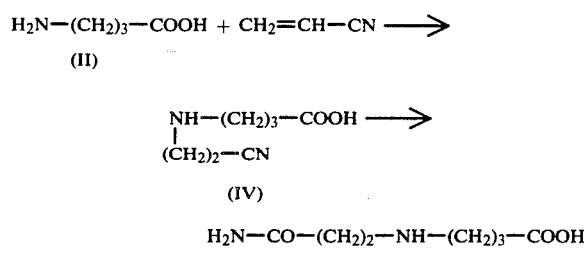

SCHEME G

Condensation of (II) or (XII) with acrylamide $CH_2=CH-CO-NH_2$ (XVI) to directly give amidoethyl-γ-aminobutyric acid (XV) or amidoethyl-γ-aminobutyramide (XIV).

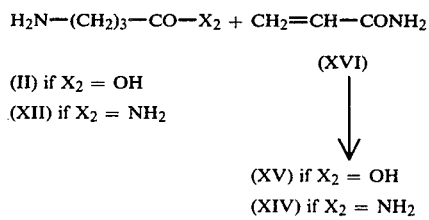

Some non-limiting examples are given hereinafter of syntheses according to the process of the invention.

EXAMPLE 1

Passage from Compound (II)' to (II)

15.5 cc of pyrrolidin-2-one (II)' are heated under reflux for one hour with 20 cc of a 40% NaOH solution.

The mixture is cooled rapidly and the product (II) used directly for the next reaction. It can be preserved for 2 or 3 days at 0° C.

EXAMPLE 2

Passage from (II) to (XI)

10.3 g of GABA (II) in 100 cc of ethanol saturated with gaseous HCl are left under reflux for 6 hours.

The mixture is evaporated to dryness under vacuum. The ester (XI) is used as such for subsequent reactions.

EXAMPLE 3

Passage from (II) to (V) via (IV)

51.5 g of GABA (II) are suspended in 50 cc of water. IRA 400 is added until the mixture is strongly basic. 30 g of acrylonitrile (III) are added slowly under agitation so that the temperature does not exceed 10° C. The mixture is left to react at ambient temperature for three hours, is then filtered and precipitated by means of acetone.

The crude product is passed through a silica gel column eluting with mixtures of $CH_2Cl_2$:MeOH of increasing polarity.

The pure product thus isolated is crystallised from methanol. 43 g of N-β-cyanoethyl-γ-aminobutyric acid (IV) are obtained, of M.P. 122°–124° C. 10 g of (IV) are dissolved in 50 cc of 37% HCl and left under reflux for one hour. The mixture is treated with anionic resin until the chlorides disappear, and then with IRC 50 until pH 3.5 is obtained, after which it is lyophilised.

9.5 g of N-β-carboxyethyl-γ-aminobutyric acid (V) are obtained of M.P. 149°–151° C.

EXAMPLE 4

Passage from (II) to (V)

51.5 g of GABA (II) are dissolved in 150 cc of 20% NaOH. 45 g of acrylic acid are added slowly so that the temperature does not exceed 10° C. The mixture is allowed to react at ambient temperature for three hours, and is then raised to 70° C., this temperature being maintained for 12 hours. The solution is treated with IRC 50 until its pH is 3.5.

The crude product is obtained by lyophilisation. The pure product is obtained by means of a silica gel column operating as in Example 3, and crystallising it from methanol. 20 g of N-β-carboxyethyl-γ-aminobutyric acid (V) are obtained, of M.P. 148°–151° C. The unreacted γ-aminobutyric acid (II) is eluted from the column by pure methanol.

EXAMPLE 5

Passage from (II) to (VIII)

51.5 g of GABA (II) are dissolved in 500 cc of MeOH containing 13 g of Na. 65 g of ethyl acrylate (VII) in 300 cc of MeOH are added slowly so that the temperature does not exceed 10° C. On terminating the addition, the mixture is heated under reflux for five hours.

After evaporating most of the solvent, the residue is taken up in $CH_2Cl_2$ and passed through a silica gel column. The fraction containing the required product is concentrated, and the product crystallised from MeOH by adding gaseous HCl. 18 g of (VIII).HCl are obtained.

EXAMPLE 6

Passage from (XI) to (IX)

The product (XI) obtained in Example 2 is added to 100 cc of MeOH containing 2 g of Na. 9 g of acrylic acid (VI) in 50 cc of MeOH are added slowly so that the temperature does not exceed 10° C. The mixture is left at ambient temperature for 12 hours. After evaporating most of the solvent, the product (IX) is taken up in $CH_2Cl_2$ and passed through a silica gel column.

The fraction containing the required product is concentrated, and the product crystallises from MeOH both as such and as the hydrochloride.

EXAMPLE 7

Passage from (XI) to (X)

The product (XI) obtained in Example 2 is treated under the same conditions as Example 6 with 13 g of ethylacrylate (VII). The product (X) crystallises from MeOH both as such and as the hydrochloride.

EXAMPLE 8

Passage from (V) to (X)

10 g of compound (V) in 100 cc of EtOH saturated with gaseous HCl are refluxed fro 6 hours. On concentrating under vacuum, the product (X) ($R_1=R_2=EtOH$) crystallises as the hydrochloride.

According to the present invention, the compounds of said general formula (I) when administered to experimental animals have demonstrated a surprising activity in their effect on the central nervous system, this being mainly of sedative type.

Experimental pharmacology and toxicology data and observations are given hereinafter by way of non-limiting example relative to one of the compounds of formula (I), namely N-β-carboxyethyl-γ-aminobutyric acid of formula (V).

PHARMACOLOGY

1. Effect on the Spinal Medulla of the Cat

At doses 3–30 mg/kg i.v. the compound (V) produces a dose-dependent reduction in the dorsal root potentials, the mono and polysynaptic reflexes of the ventral root, and the activity on the gamma-mononeuron.

2. Effect on the cGMP Levels in the Rat Cerebellum

At doses of 10,30 and 100 mg/kg i.v., compound (V) significantly reduces the cGMP in the rat cerebellum ($-30$, $-40\%$). The cGMP is measured 1 hour after administration.

The data are given in the following table.

| Dose | No. Animals | cGMP: Relative levels |
|---|---|---|
| Saline, i.v. | 12 | 100 |
| 1 mg/kg, i.v. | 8 | 95 ± 8 |
| 10 mg/kg, i.v. | 12 | 68 ± 4 |
| 30 mg/kg, i.v. | 6 | 60 ± 5 |
| 100 mg/kg, i.v. | 6 | 74 ± 6 |

3. EEG in Rabbits

At doses of 100 and 50 mg/kg i.v., electrical activity becomes evidently synchronous 10 minutes after administration, and lasts for about 3 hours. Basal activity is replaced by a slow continuous activity prevalent on the cortical graph. The thalamus and hippocampus growth also shows modifications the activity at 4–5 Hz which is commonly present is replaced by an irregular graph and many slow waves. Vibro-stimulation and pain stimuli do not desynchronise cortical activity. The animal is sedated, but responds to stimuli. After 4 hours, behaviour and EEG become normal.

In conclusion, the active compound overcomes the hematoencephalic barrier and demonstrates sedative activity.

4. Effect of Compound (V) Administered Intravenously to the Rat, on the Plasmatic Prolactin Levels (PRL)

The compound when administered intravenously to the rat shows a dose-dependent effect on the prolactin release at short intervals after administration.

| Dose | PRL levels (mg/ml) at | | | |
|---|---|---|---|---|
| | 0 min | 15 min | 30 min | 60 min |
| Controls (saline) | 4 | 4 ± 1 | 10 ± 6 | 4 |
| 100 mg/kg | 4 | 18 ± 5 | 4 ± 6 | 4 |
| 200 mg/kg | 4 | 49 ± 10 | 5 ± 1 | 4 |
| 300 mg/kg | 4 | 78 ± 5 | 21 ± 8 | 12 |

TOXICOLOGY

Mutagenesis (salmonella thyphimurium, 5 different strains): 1000-100-10 mcg/plate: negative. Genetic conversion (Sacch. cerevisiae D4): 1000-100-10 mcg/plate: doubtful; a slight increase in mutagenic activity is observed for the gene TPR 5 (not for the gene ADE 2), only when in the presence of a microsomial activator.

Generic mutation (Schizosacch. pombe P1): 1000-100-10 mcg/plate: negative. Mutagenic metabolites (urine test, S. cerevisiae D4): 300 and 30 mg/kg/day i.p.: negative. Mutagenic mediated host metabolites (S. cerevisiae D4): 300 and 30 mg/kg s.c.: negative.

| ACUTE TOXICITY | DL50 | |
| --- | --- | --- |
| Administration | Rat | Mouse |
| oral (+) | 1 g/kg | 1 g/kg |
| intra-peritoneal (++) | 877 mg/kg | 783 mg/kg |
| (+) | 1 g/kg | 1 g/kg |
| Observation period: 14 days | | |

(+) from 500 mg/kg upwards, the animals show sedation symptoms.
(++) ataxia, lack of reaction to stimuli, and dyspnea are observed before death.

SUB-ACUTE TOXICITY

After daily oral and intra-peritoneal administration of 10,20 and 40 mg/kg/day of compound (V) for 4 weeks, no effect is observed on mortality, body weight, alimentation, hematological or urinary data, autoptic examination, weight or histology of the organs.

As stated, the compounds of formula (I) according to the invention can be used advantageously for sedative and tranquillising purposes in both the medical and veterinary field, in suitable compositions in which said compounds are contained as active principles preferably in the following proportions:

| (A) Human use Administration: | |
| --- | --- |
| oral | 4–20 mg/kg/day |
| parenteral | 1–10 mg/kg/day |
| rectal | 2–20 mg/kg/day |
| (B) Veterinary use | 2–20 mg/kg/day |

We claim:
1. A method of inducing a tranquilizing activity in a subject in need of same comprising administering to said subject a tranquilizing amount of a compound of the formula:

$$X_1OC-(CH_2)_2-NH-(CH_2)_3-CO-X_2$$

in which $X_1$ and $X_2$ are hydroxyl, a $C_1$–$C_6$ alkoxy group or a free amino group.

2. A method according to claim 1 where $X_1$ and $X_2$ are both hydroxyl.

* * * * *